(12) United States Patent
Hung

(10) Patent No.: US 12,708,801 B2
(45) Date of Patent: Aug. 18, 2026

(54) FIXING DEVICE FOR BREATHING TUBE

(71) Applicant: Wei-Cheng Hung, Taipei City (TW)

(72) Inventor: Wei-Cheng Hung, Taipei City (TW)

( * ) Notice: Subject to any disclaimer, the term of this patent is extended or adjusted under 35 U.S.C. 154(b) by 2200 days.

(21) Appl. No.: 15/701,556

(22) Filed: Sep. 12, 2017

(65) Prior Publication Data

US 2018/0071556 A1 Mar. 15, 2018

(30) Foreign Application Priority Data

Sep. 14, 2016 (TW) ............................ 105214257 U

(51) Int. Cl.
*A62B 9/04* (2006.01)
*A61M 16/08* (2006.01)
*A61M 39/08* (2006.01)
*A61M 39/10* (2006.01)

(52) U.S. Cl.
CPC ........... *A62B 9/04* (2013.01); *A61M 16/0875* (2013.01); *A61M 39/08* (2013.01); *A61M 39/1011* (2013.01); *A61M 2039/087* (2013.01); *A61M 2209/08* (2013.01)

(58) Field of Classification Search
CPC ..... A62B 9/04; A61M 16/0497; A61M 39/08; A61M 2039/087; A61M 39/12; A61M 2209/088
USPC ........................... 128/207.11, 206.27, 207.17
See application file for complete search history.

(56) References Cited

U.S. PATENT DOCUMENTS 3,760,811 A * 9/1973 Andrew ................ A61M 25/02 128/207.17
6,578,576 B1 * 6/2003 Taormina .......... A61M 16/0488 128/200.24
7,445,293 B2 * 11/2008 Smith ................. B60N 2/2812 24/614
8,978,656 B2 * 3/2015 Chien .................... A62B 18/08 128/207.11
2002/0189614 A1 * 12/2002 Dominguez ...... A61M 16/0488 128/200.26
2005/0188993 A1 * 9/2005 Steeves ............... A61M 16/047 128/207.17
2011/0146685 A1 * 6/2011 Allan .................... A61M 16/06 128/205.25

* cited by examiner

*Primary Examiner* — Kristen Matter

(57) ABSTRACT

A fixing device is applied to fix a breathing tube which includes a free segment located outside a patient, and the fixing device contains: a strap, a connector, and a fixer. The strap has two opposite ends, and each end is provided with a hooks-fastener portion and a loops-fastener portion. The connector defines a first slit and a second slit. Each end of the strap can be inserted through one of the slits to have the loops-fastener portion joined with the hooks-fastener portion, so that the strap is connected with the connector and formed into a collar capable of surrounding a patient's neck. The fixer includes a base mounted on the connector and includes two arms extending outwardly from the base so that the free segment of the breathing tube is clamped by the two arms.

2 Claims, 6 Drawing Sheets

FIXING DEVICE FOR BREATHING TUBE

FIELD OF THE INVENTION

The present invention relates to a fixing device, and the fixing device being applied to fix a breathing tube which includes a free segment located outside a patient.

BACKGROUND OF THE INVENTION

A conventional breathing tube, such as a tracheal tube, is usually employed to help a patient to breathe well.

However, when the patient turns on the bed or gets up from the bed, the breathing tube drops to the ground easily.

The present invention has arisen to mitigate and/or obviate the afore-described disadvantages.

SUMMARY OF THE INVENTION

The primary objective of the present invention is to provide a fixing device which is applied to securely fix a breathing tube which includes a free segment located outside a patient.

To achieve the above objective, a fixing device generally comprises a strap, a connector, and a fixer.

The connector defines a first slit and a second slit. The strap has two opposite ends, and each end is provided with a hooks-fastener portion and a loops-fastener portion. Each end of the strap can be inserted through one of the slits of the connector to have the loops-fastener portion joined with the hooks-fastener portion, so that the strap is formed into a collar capable of surrounding a patient's neck.

The fixer includes a base mounted on the connector and includes two arms extending outwardly from the base so that the free segment of the breathing tube is clamped by the two arms.

DETAILED DESCRIPTION OF THE FIRST EMBODIMENTS

Figure 1:
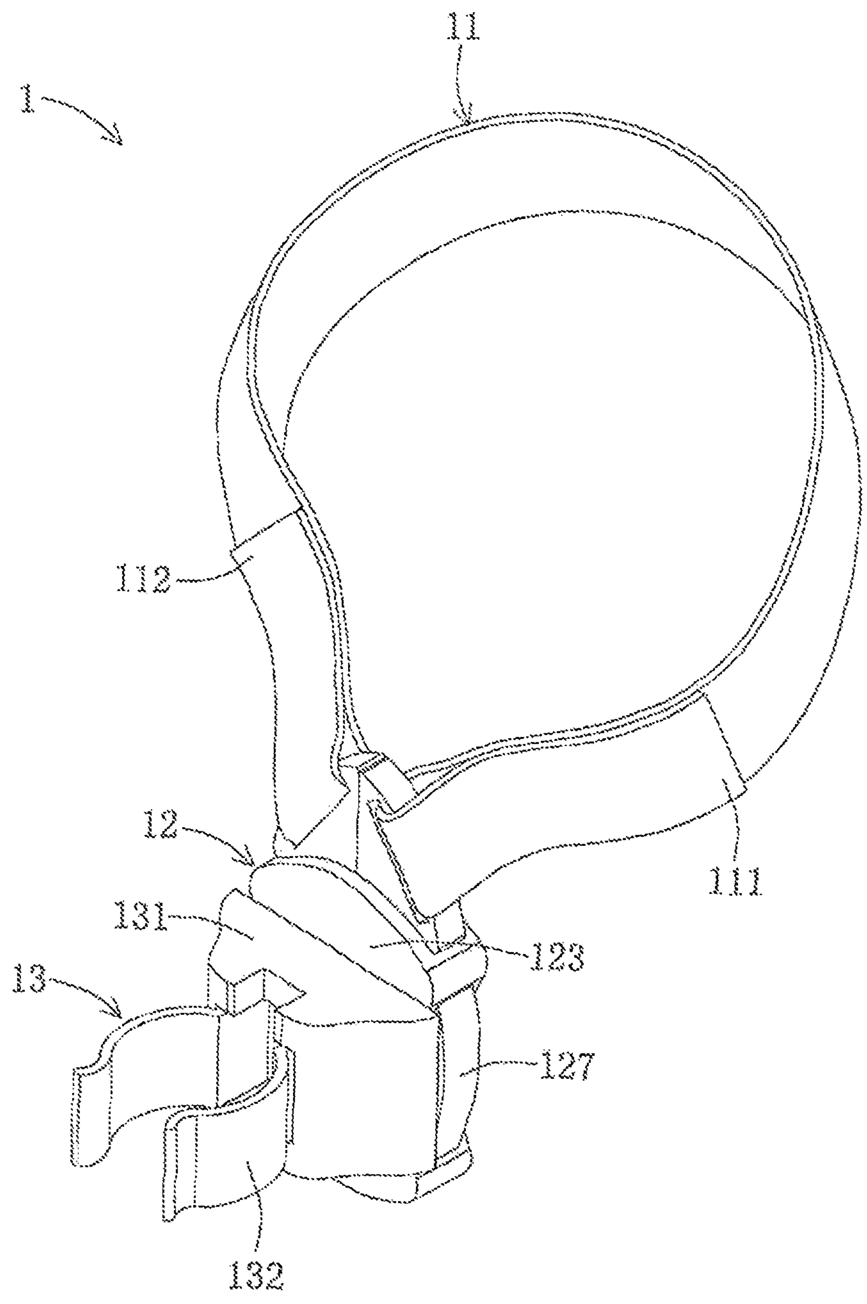
FIG. 1 is a perspective view showing the assembly of a fixing device for a breathing tube according to a first embodiment of the present invention, wherein the fixing device generally comprises a strap, a connector, and a fixer.
Figure 2:
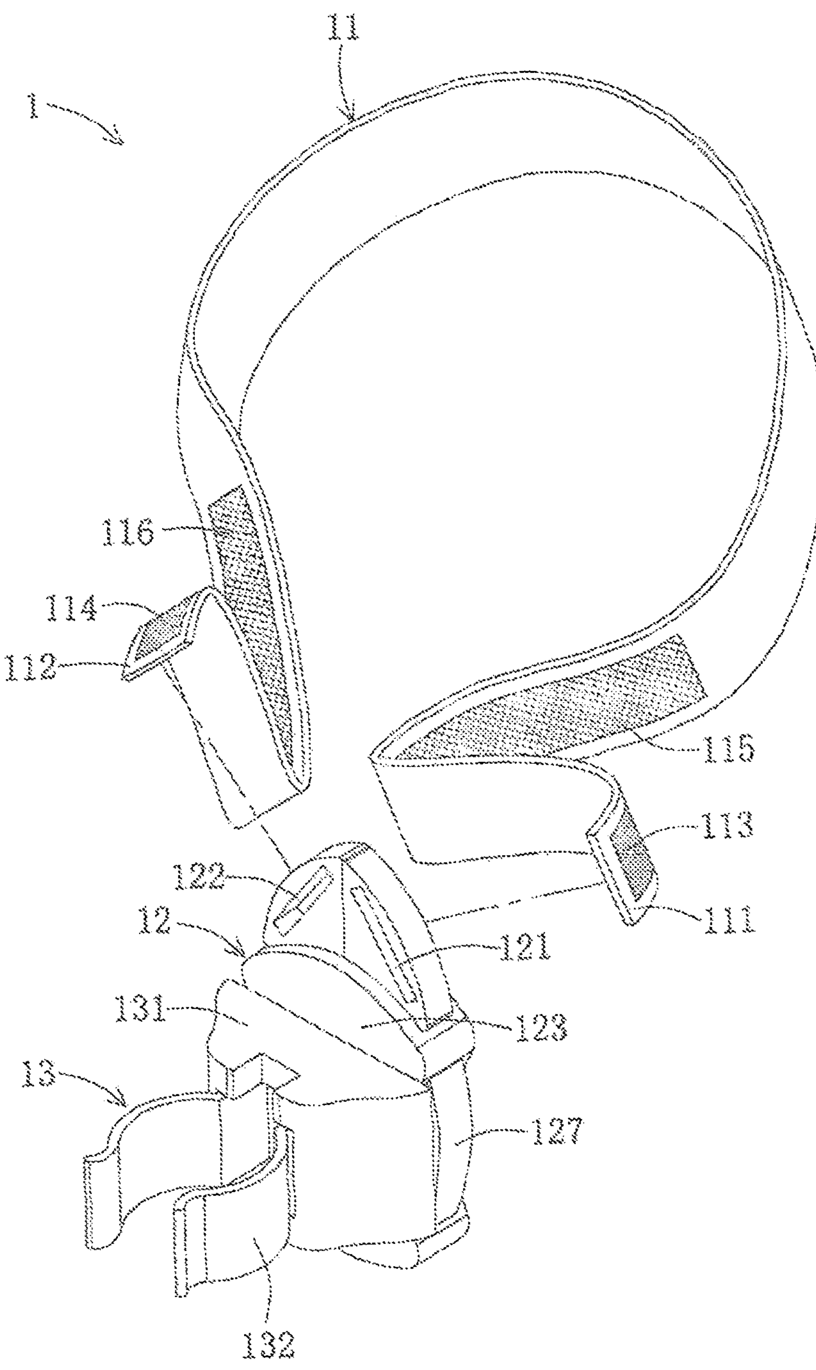
FIG. 2 is a perspective view of the fixing device, wherein the strap is detached from the connector.

With reference to FIGS. 1-6, a fixing device 1 according to a first embodiment of the present invention is applied to fix a breathing tube 100 which includes a free segment 101 located outside a patient. The fixing device 1 generally comprises a strap 11, a connector 12, and a fixer 13.

The strap 11 has a first end 111 and a second end 112 opposite to the first end 111, wherein the strap 11 is made of a flexible, air-permeable material.

Figure 3:
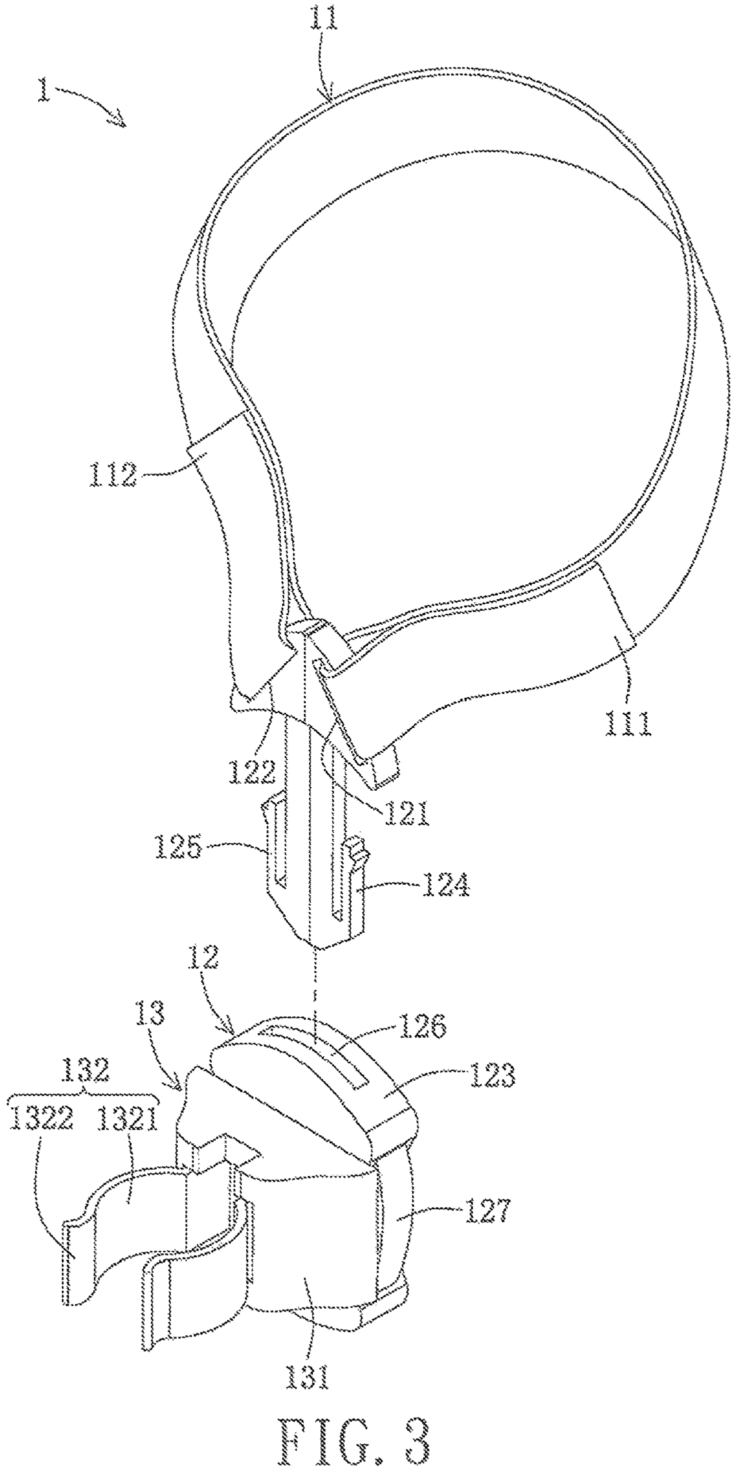
FIG. 3 is a perspective view of the fixing device, wherein the connector is disassembled.
Figure 4:
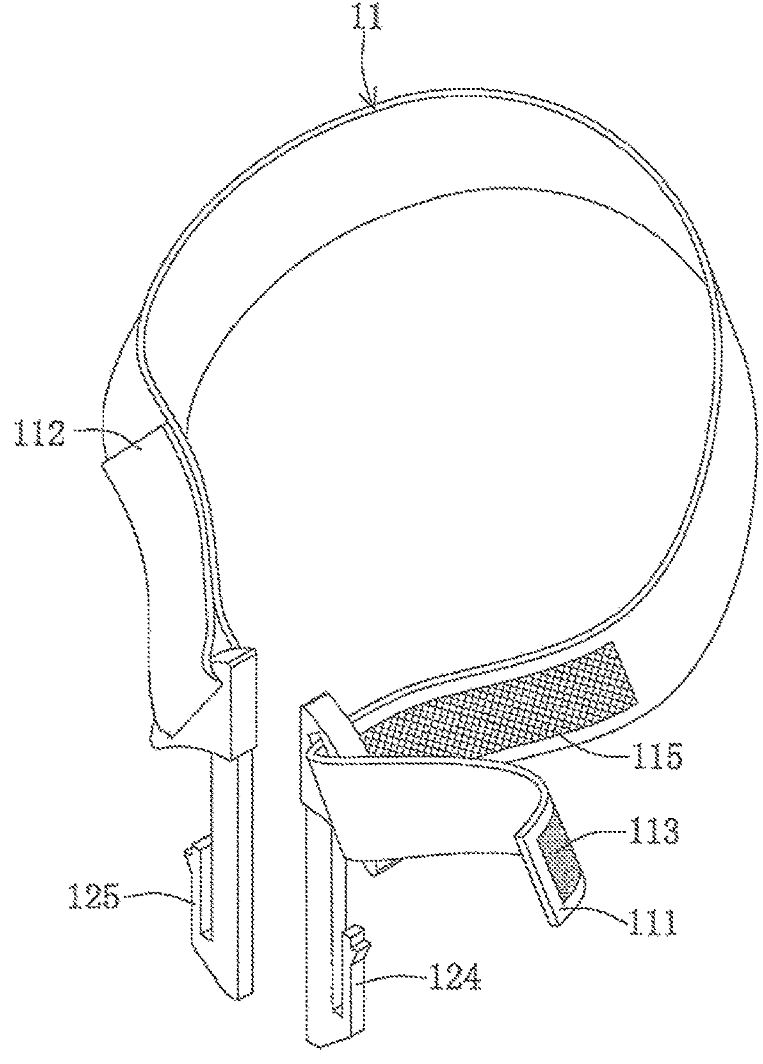
FIG. 4 is a perspective view showing the strap and parts of the connector used in the fixing device.

In this embodiment, the connector 12 is constructed of a first body, a second body, and a third body 123. The first body defines a first slit 121 at its top and has a first retainer 124 formed at its bottom; the second body defines a second slit 122 and has a second retainer 125 formed at its bottom (as shown in FIG. 3), wherein the first end 111 and the second end 112 of the strap 11 respectively insert through the first slit 121 and the second slit 122 so as to connect with the connector 12. The strap 11 is provided at the first end 111 with a first loops-fastener portion 113 and a first hooks-fastener portion 115 adjacent to and corresponding to the first loops-fastener portion 113. On the other hand, the strap 11 is provided at the second end 112 with a second loops-fastener portion 114 and a second hooks-fastener portion 116 adjacent to and corresponding to the second loops-fastener portion 114. The strap 11 allows its two ends 111, 112 to be inserted through the slits 121, 122 respectively, and each inserted part of the strap 11 can be folded back to have the first loops-fastener portion 113 joined with the first hooks-fastener portion 115, and to have the second loops-fastener portion 114 joined with the second hooks-fastener portion 116. As such, the strap 11 is formed into a collar, which can be adjusted in size to surround a patient's neck.

The third body 123 defines a locking groove 126 at a top thereof (as illustrated in FIG. 3) so that the first retainer 124 and the second retainer 125 can be received in the locking groove 126 and locked therein. The third body 123 is provided with two press buttons 127 at two sides thereof, engageable with the first and second retainers 124, 125, such that the two press buttons 127 can be depressed to force the first retainer 124 and the second retainer 125 to remove from the third body 123 quickly.

Figure 5:
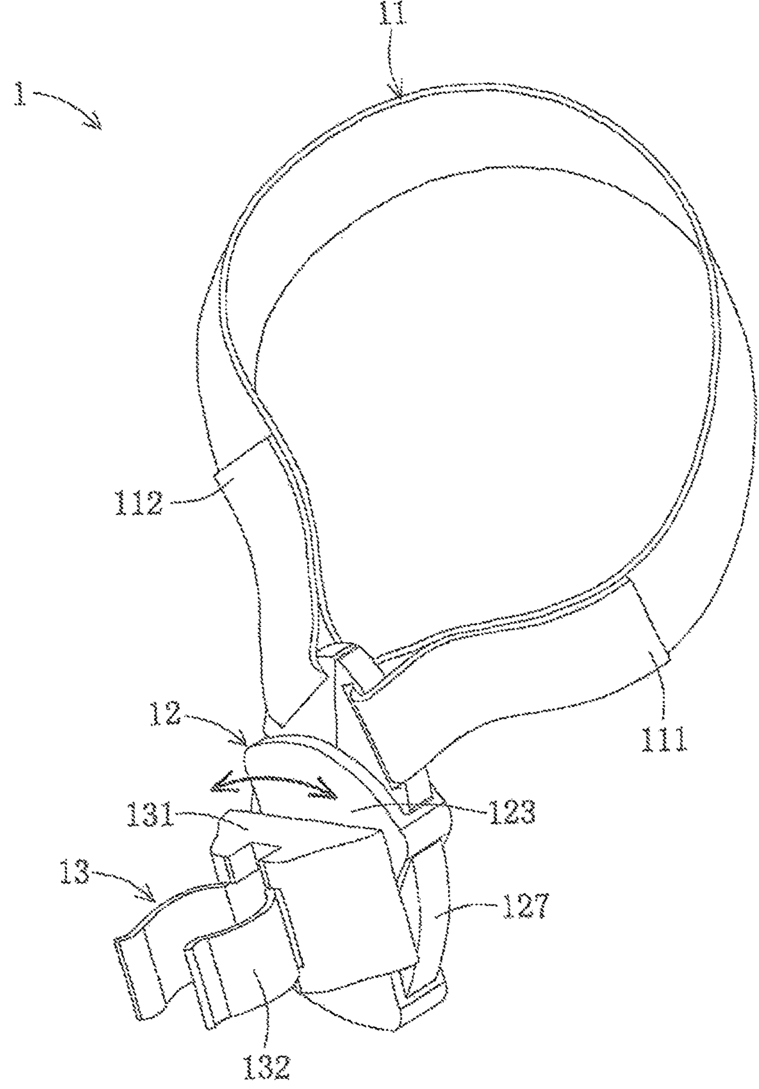
FIG. 5 is a perspective view of the fixing device, wherein the fixer is adjusted to be at an angle to the connector.

The fixer 13 includes a base 131 mounted on the connector 12 and includes two arms 132 extending outwardly from the base 131 so that the free segment 101 of the breathing tube 100 is clamped by the two arms 132 securely. Each of the two arms 132 is flexible and configured to have an inwardly curved section 1321 next to the base 131, and an outwardly curved section 1322 distal from the base 131. The outwardly curved section 1322 can guide the free segment 101 of the breathing tube 100 to move into a space between the two arms 132. The inwardly curved sections 1321 of the two arms 132 flexibly clamp the free segment 101 of the breathing tube 100. In this embodiment, the base 131 of the fixer 13 is mounted at a front of the third body 123. In another embodiment, the base 131 is rotatably connected with the third body 123 of the connector 12 (as shown in FIG. 5), hence the breathing tube 100 can be adjusted at a desired angle.

Figure 6:
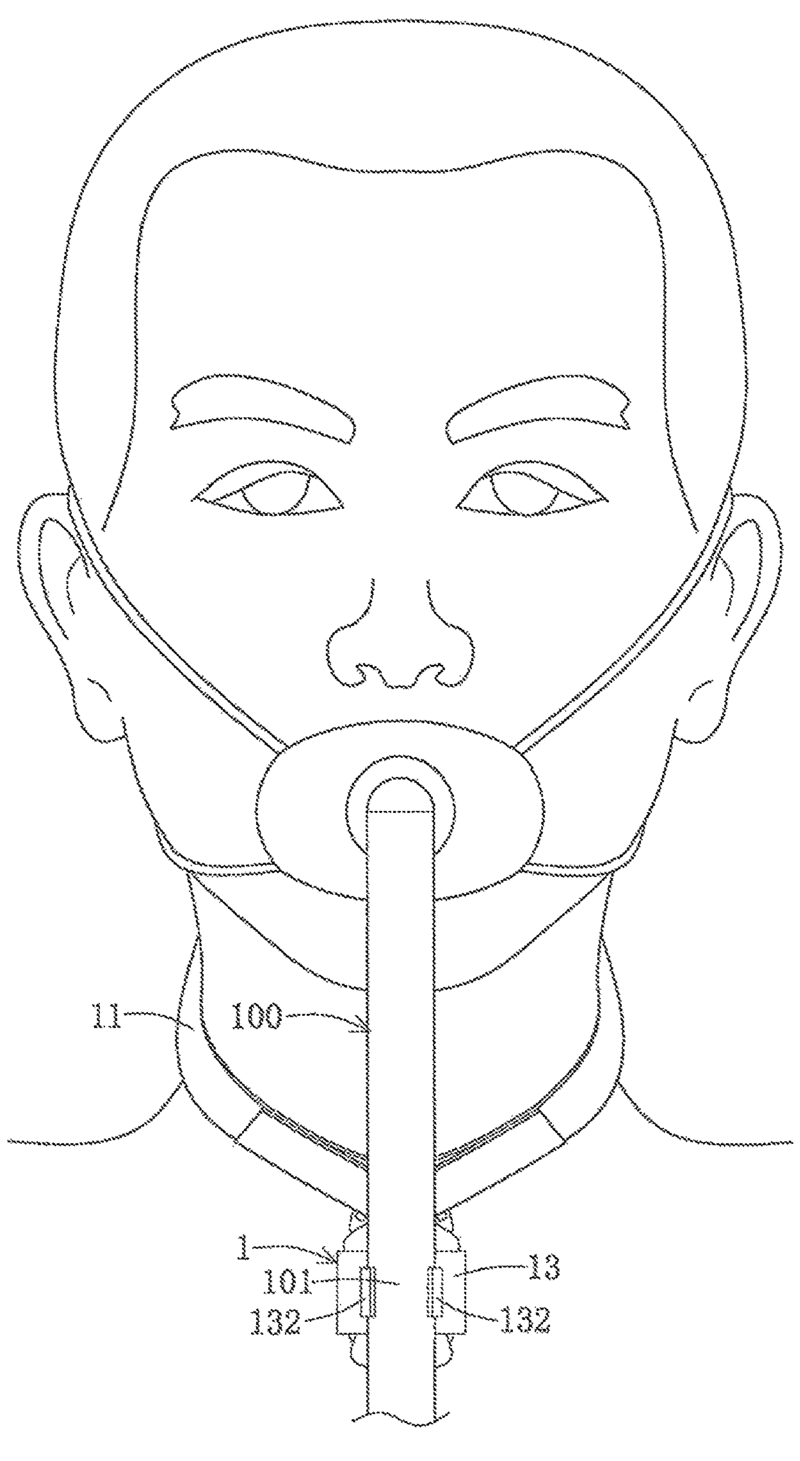
FIG. 6 is a perspective view showing the fixing device being applied to fix a breathing tube.

Referring further to FIG. 6, in use, the adjustable collar 11 of the fixing device 1 surrounds the neck of a patient, and the fixer 13 of the fixing device 1 is located between the neck and a chest of the patient so that the free segment 101 of the breathing tube 100 is fixed by the fixer 13 to locate between the neck and the chest of the patient securely.

While the embodiments of the invention have been set forth for the purpose of disclosure, modifications of the disclosed embodiments of the invention as well as other embodiments thereof may occur to those skilled in the art. The scope of the invention should not be limited by the embodiments set forth in the examples.

What is claimed is:

1. A fixing device for breathing tubes comprising a connector, a strap, and a fixer; wherein the connector defines a first slit and a second slit; the strap is made of a flexible, air-permeable material and has two opposite ends, each end provided with a hooks-fastener portion and a loops-fastener portion and capable of being inserted through one of the first and second slits of the connector to have the hooks-fastener portion joined with the loops-fastener portion, so that the strap is connected to the connector and formed into a collar that is adjustable in size to surround a patient's neck; the fixer has a base and two arms extending from the base and defining a space therebetween, the base being mounted to the connector, each of the two arms configured to have an inwardly curved section next to the base, and an outwardly curved section distal from the base; and wherein the connector is constructed of a first body, a second body, and a third body, the first slit defined at a top of the first body, the second slit defined at a top of the second body, the first body having a first retainer formed at a bottom thereof, the second body having a second retainer formed at a bottom thereof, the third body defining a locking hole to receive the first and second retainers of the first and second bodies, and provided at two opposite sides thereof with two press buttons engageable with the first and second retainers respectively, the base of the fixer mounted at a front of the third body, whereby the first and second bodies are detachably joined to the third body by inserting the first and second retainers thereof into the locking hole of the third body.

2. The fixing device as claimed in claim 1, wherein the base of the fixer is rotatably mounted at the front of the third body.

* * * * *